US008065164B2

(12) United States Patent
Hwang

(10) Patent No.: US 8,065,164 B2
(45) Date of Patent: Nov. 22, 2011

(54) METHOD AND SYSTEM FOR MANAGING OF ORAL CARE

(75) Inventor: Jin-Sang Hwang, Suwon-si (KR)

(73) Assignee: Xiusolution Co., Ltd., Yongin-Si (KR)

( * ) Notice: Subject to any disclaimer, the term of this patent is extended or adjusted under 35 U.S.C. 154(b) by 797 days.

(21) Appl. No.: 11/919,741

(22) PCT Filed: Jun. 19, 2006

(86) PCT No.: PCT/KR2006/002341
§ 371 (c)(1),
(2), (4) Date: Nov. 1, 2007

(87) PCT Pub. No.: WO2006/137661
PCT Pub. Date: Dec. 28, 2006

(65) Prior Publication Data
US 2009/0130636 A1 May 21, 2009

(30) Foreign Application Priority Data

Jun. 20, 2005 (KR) .......................... 10-2005-0053267
Nov. 15, 2005 (KR) .......................... 10-2005-0108830

(51) Int. Cl.
*G06Q 50/00* (2006.01)

(52) U.S. Cl. ..................................... 705/2; 705/4; 705/3
(58) Field of Classification Search ................... 705/2–4
See application file for complete search history.

(56) References Cited

U.S. PATENT DOCUMENTS

| 4,716,614 A * | 1/1988 | Jones et al. .................... 15/105 |
| 6,611,780 B2 * | 8/2003 | Lundell et al. ................. 702/122 |
| 2003/0158758 A1 * | 8/2003 | Kanazawa et al. ................ 705/4 |

* cited by examiner

*Primary Examiner* — Gerald J. O'Connor
*Assistant Examiner* — Sind Phongsvirajati
(74) *Attorney, Agent, or Firm* — Staas & Halsey LLP

(57) ABSTRACT

In a system and a method for managing of oral care, tooth brushing (pattern) data is received whenever a user brushes his or her teeth using a tooth brushing correction toothbrush. The received tooth brushing (pattern) data is recorded in a tooth brushing pattern database. The recorded tooth brushing (pattern) data is analyzed with reference to information of the user. An adaptability of the user according to the analyzed result is determined. Tooth brushing correction multimedia contents are chosen in response to the determined adaptability. The chosen tooth brushing correction multimedia contents are provided for the user. Thus, tooth brushing habits of the user may be corrected, a timely dental appointment may be made, and dental hygiene equipment may be replaced in time. Further, an oral health-related insurance rate may be accurately calculated.

11 Claims, 8 Drawing Sheets

METHOD AND SYSTEM FOR MANAGING OF ORAL CARE

CROSS-REFERENCE TO RELATED APPLICATIONS

This application claims the benefit of Korean Application Nos. 10-2005-0053267, filed Jun. 20, 2005, in the Korean Intellectual Property Office, and 10-2005-0108830, filed Nov. 15, 2005 and PCT Application No, PCT/KR2006/002341, filed Jun. 19, 2006, the disclosure of which is incorporated herein by reference.

BACKGROUND

1. Field

An aspect of one or more embodiments relate to a method and a system for managing of oral care, and more particularly, to a method and a system for managing of oral care in which a user may be guided to acquire correct tooth brushing habits by collecting data for the user's tooth brushing habits online and analyzing the data, and may be provided with oral health-related information.

2. Description of the Related Art

The South Korean government has enacted oral health measures in order to improve national oral health, and raised funds by imposing health promotion fees on cigarettes to use in managing oral health and performing research on improving oral health.

However, oral health work, for example, research and education for oral health, tap water fluoridation, oral health work in schools, oral health work in workplaces, oral health work for old persons and handicapped persons, oral health work for pregnant women and infants, etc., has mainly been performed offline until now, so that efficiency of the oral health work has been low in consideration of the amount of time, funds, and the number of persons used in performing the oral health work.

Additionally, oral health-related data is independently made according to respective types of work performed, so that a complete database for the oral health-related data may not be easily made.

Further, collecting data offline is normally performed by a questionnaire, so that errors may exist according to a level of respondent participation for the questionnaire. Thus, accurate data analysis may be difficult, so that reliability of the data may be low.

Furthermore, oral health-related public relations (PR) brochures or data is produced to reflect average levels and are distributed widely, so that a user may not be able to easily get proper information suited for the user through the brochures or the data, even though the brochures or the data contain general information.

Furthermore, a user typically does not go to a dentist until the user has a toothache because of time and costs, so that only very few persons regularly receive diagnoses and therapy from a dentist. Thus, effective prevention of oral diseases is not being made.

Therefore, a system is required in which a database for oral health may be constructed through systematic and reliable data collection and accurate analysis.

SUMMARY

Additional aspects and/or advantages will be set forth in part in the description which follows and, in part, will be apparent from the description, or may be learned by practice of the invention.

Technical Problem

An embodiment provides a method and a system for managing oral health, in which multimedia contents for interactively teaching a user correct tooth brushing methods may be provided in real-time.

Another embodiment also provides a method and a system for managing oral health in which a user's tooth brushing period may be naturally elongated by providing the user with multimedia contents suited to the user's interests during the tooth brushing.

An embodiment still also provides a method and a system for managing oral health in which a user's adaptability may be enhanced in order that the user may acknowledge how important correct tooth brushing habits are by providing data showing in real-time bad effects of bad tooth brushing habits.

An embodiment further still also provides a method and a system for managing oral health in which a user's lifelong state of dental health may be monitored by making a database for analyzed results of the user's (daily) tooth brushing habits.

An embodiment further still also provides a method and a system for managing oral health in which a user's tooth brushing habits and the user's state of dental health may be transferred to an oral health center connected to the user's system online so that remote consulting for oral health may be made.

An embodiment further still also provides a method and a system for managing oral health in which a dental appointment may be made when a dental treatment is needed, according to a user's tooth brushing habits.

An embodiment further still also provides a method and a system for managing oral health in which a replacement time of dental hygiene equipment may be determined according to a user's tooth brushing habits, and the dental hygiene equipment may be purchased.

An embodiment herein further still also provides a method and a system for managing oral health in which information with regard to fluctuation of an insurance rate may be provided according to a user's adaptability related to tooth brushing habits.

Technical Solution

According to one of the embodiments, a method for managing oral health provides a multimedia tooth brushing correction program. In the multimedia tooth brushing correction program, tooth brushing pattern data is received when a user brushes his or her teeth using a tooth brushing correction toothbrush. The received tooth brushing pattern data is recorded in a tooth brushing pattern database. The recorded tooth brushing pattern data is analyzed with reference to information of the user. An adaptability of the user is determined according to the analyzed result. Tooth brushing correction multimedia contents are chosen in response to the determined adaptability. The chosen tooth brushing correction multimedia contents are provided for the user.

Thus, the tooth brushing correction multimedia contents are fed back in response to the user's tooth brushing habits, and the adaptability of the user is evaluated so that the user may be lead into correcting the user's tooth brushing habits.

In accordance with an example embodiment, the tooth brushing pattern data may include at least one of a user's tooth brushing time, tooth brushing period, tooth brushing frequency, tooth brushing angle, tooth brushing pattern, and tooth brushing period of each teeth region. Here, the tooth brushing period of each teeth region may include a lower incisor region, a lower left molar region, a lower right molar region, an upper incisor region, an upper left molar region, an upper right molar region, etc. For more particular analysis, each of the lower incisor region, the lower left molar region, the lower right molar region, the upper incisor region, the upper left molar region and the upper right molar region may be divided into an outer portion and an inner portion.

In accordance with an example embodiment, the information of the user may include user's age, sex, address, occupation, scheduled next visit, clinical history, dental treatment status, etc.

According to another aspect of the embodiment, there is provided a method of managing oral health. In the method of managing oral health, tooth brushing pattern data generated when a user uses a tooth brushing correction toothbrush is received. The received tooth brushing pattern data is recorded in a tooth brushing pattern database. The recorded tooth brushing pattern data is analyzed with reference to information of the user. Whether a dental treatment for the user is needed or not is determined according to the analyzed result. Information of a treatment hospital and an available appointment time of the treatment hospital are provided for the user when the dental treatment for the user is needed. An appointment for the user at the appointment time in the treatment hospital chosen by the user is processed in response to the provided information.

According to still another embodiment, there is provided a method of managing oral health. In the method of managing oral health, tooth brushing (pattern) data generated when a user uses a tooth brushing correction toothbrush is received. The received tooth brushing (pattern) data is recorded in a tooth brushing pattern database. The recorded tooth brushing (pattern) data is analyzed with reference to information of the user. A replacement time of dental hygiene equipment of the user is determined according to the analyzed result. Information of a suitable product is provided for the user when the dental hygiene equipment needs to be replaced. Purchasing of a product, wherein the product is chosen by the user among the products whose information is provided for the user, is processed.

According to further still another embodiment, there is provided a method of managing oral health. In the method of managing oral health, tooth brushing pattern data generated when a user uses a tooth brushing correction toothbrush is received. The received tooth brushing (pattern) data is recorded in a tooth brushing (pattern) database. The recorded tooth brushing (pattern) data is analyzed with reference to information of the user. A probability of an insurance rate increase is determined according to the analyzed result. The user is warned of the probability of the insurance rate increase when the insurance rate is expected to increase by the determination. An adaptability of the user is calculated by analyzing the tooth brushing pattern data and enrollment conditions. An insurance rate is calculated in response to the adaptability. The calculated insurance rate is provided for the user.

Effect of the Invention

According to an embodiment, a user's tooth brushing pattern may be analyzed in real-time and whether a dental treatment is needed or not may be automatically advised to the user based on the analysis. Further, a dental appointment may be made online.

Additionally, from a dentist's standpoint, the dentist may easily know a patient's tooth brushing pattern so that dental treatment may be improved, and dental disease may be prevented from occurring by allowing the dentist to understand a cause of the patient's toothache or other symptoms, and correct the patient's tooth brushing pattern.

When a system for improving oral health according to an embodiment is used, a real-time or remote feedback that is suitable for correcting a user's tooth brushing pattern may be performed so that correcting the user's behavior may be very effective. Further, a remote feedback of a correcting method suitable for each user may be performed by analyzing accumulated data for the user so that the correction function may be improved.

Furthermore, according to an embodiment, a child may develop an interest in correct tooth brushing habits, and an adult may analyze the adult's tooth brushing habits and correct bad tooth brushing habits by a real-time or remote feedback. The adult may be also advised of a replacement time of toothbrush bristles and an insurance rate according to the adult's tooth brushing habits, so that the adult may manage oral health together with a toothbrush seller, a toothbrush manufacturer and an insurance company, and efficiency of oral health work may be enhanced. Also, the system according to the embodiment may be a new income source for a dentist.

BRIEF DESCRIPTION OF THE DRAWINGS

The above and other advantages of the embodiments will become more apparent by describing in detail example embodiments thereof with reference to the accompanying drawings, in which:

FIG. 3 is an example feedback data;

DETAILED DESCRIPTION OF THE EMBODIMENTS

Figure 1:
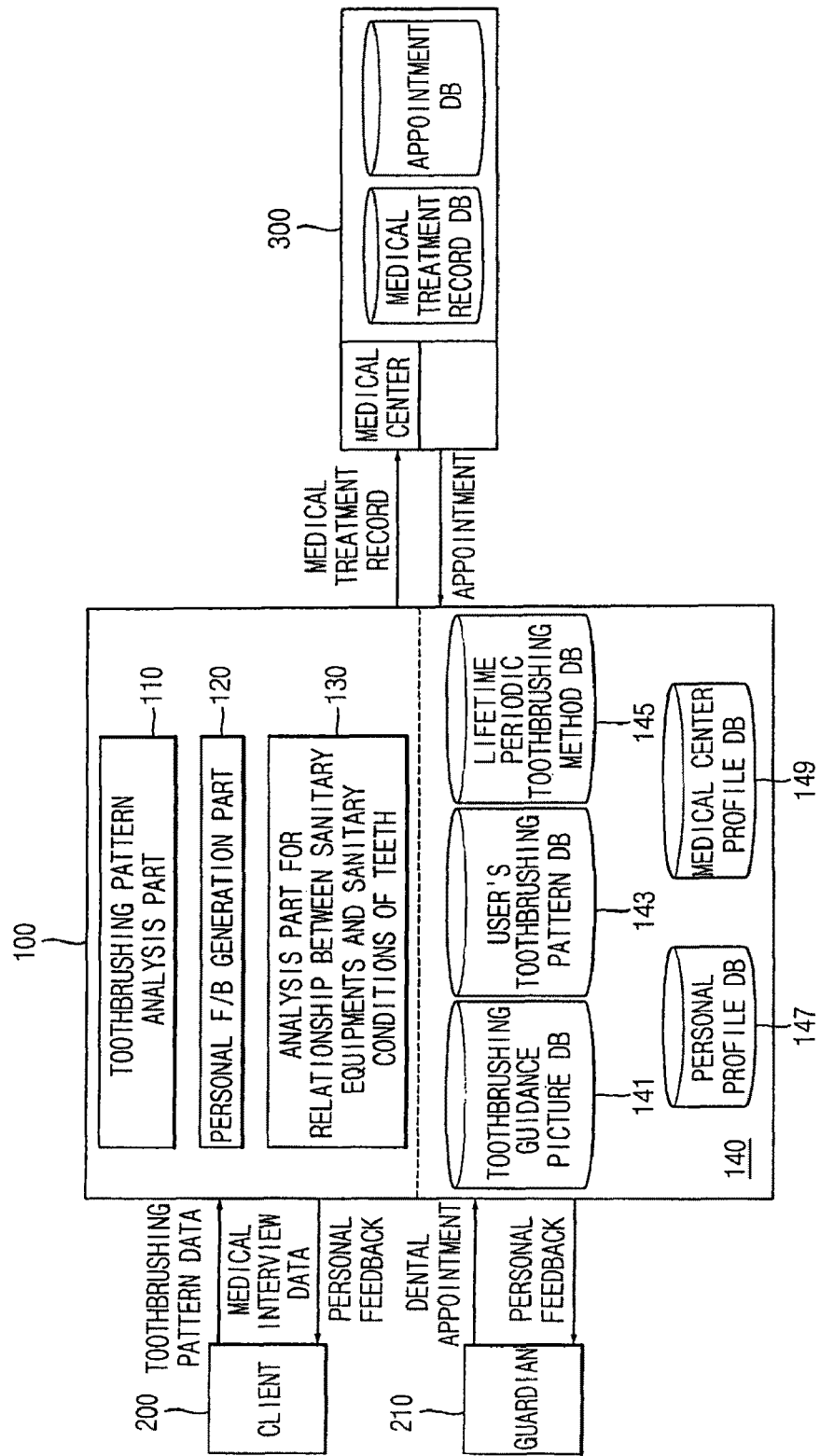
FIG. 1 is a block diagram of a system for tooth brushing correction and dental appointment in accordance with an example embodiment.

Reference will now be made in detail to the embodiments, examples of which are illustrated in the accompanying drawings, wherein like reference numerals refer to the like elements throughout. The embodiments are described below to explain the present invention by referring to the figures.

BEST MODE FOR CARRYING OUT THE INVENTION

It should be understood that the example embodiments described below may be varied modified in many different ways without departing from the inventive principles disclosed herein, and the scope of the present invention is therefore not limited to these particular following embodiments. Rather, these embodiments are provided so that this disclosure will be through and complete, and will fully convey the concept of the invention to those skilled in the art by way of example and not of limitation.

Hereinafter, one or more embodiment will be described in detail with reference to the accompanying drawings.

According to some example embodiments, a system for managing oral health basically receives a user's tooth brushing (pattern) data from a user's system in real-time and analyzes the received data so that the system may provide the user's system with multimedia contents for correcting the user's tooth brushing habits, which leads the user into enhancing the user's tooth brushing habit adaptability, in response to the user's adaptability.

The system may perform three application programs, that is, a dental appointment program, a replacement management system for hygiene equipment, and an insurance management system for oral health with the above program for correcting the user's tooth brushing habits, as follows.

1. System for Tooth Brushing Correction and Dental Appointment

FIG. 1 is a block diagram of a system for tooth brushing correction and dental appointment in accordance with an example embodiment.

Referring to FIG. 1, a system 100 for tooth brushing correction and dental appointment receives tooth brushing pattern data from a client's system or a user's system 200 in real-time and analyzes the received data so that the system 100 may provide personal feedback data for the user and a guardian 210. The client's system or the user's system 200 is a system for tooth brushing habit correction disclosed in Korean Patent Application Nos. 2005-108830 and 2005-53267, which was applied for by this applicant, and includes a tooth brushing pattern analysis/correction device and a smart bath. The smart bath includes a smart mirror, and multimedia contents for tooth brushing correction may be displayed to a user through the smart mirror. Additionally, the system 100 receives medical records from a medical center system 300, and transfers appointment data to the medical center system 300. The medical center system 300 includes a medical center computer system or an affiliated hospital computer system connected to the Internet, and includes an application program installed therein for communicating with the system 100. The medical center system 300 contains a medical record database and an appointment database. The medical center system 300 uploads data including consultation hours, appointment state, etc., to the system 100 and downloads medical appointment data in real-time.

The system 100 includes a tooth brushing pattern analysis part 110, a personal feedback data generation part 120 and a database part 140. The database part 140 includes a tooth brushing guidance picture database 141, a user's tooth brushing pattern database 143, a lifetime periodic tooth brushing method database 145, a personal profile database 147 and a medical center profile database 149.

The tooth brushing guidance picture database server 141 may be constructed with tooth brushing guidance multimedia contents. The multimedia contents may include tooth-related multimedia data, such as guiding picture data according to teeth region and age, tooth management guiding picture data according to lifetime period, dental clinic case picture data, etc.

Figure 2:
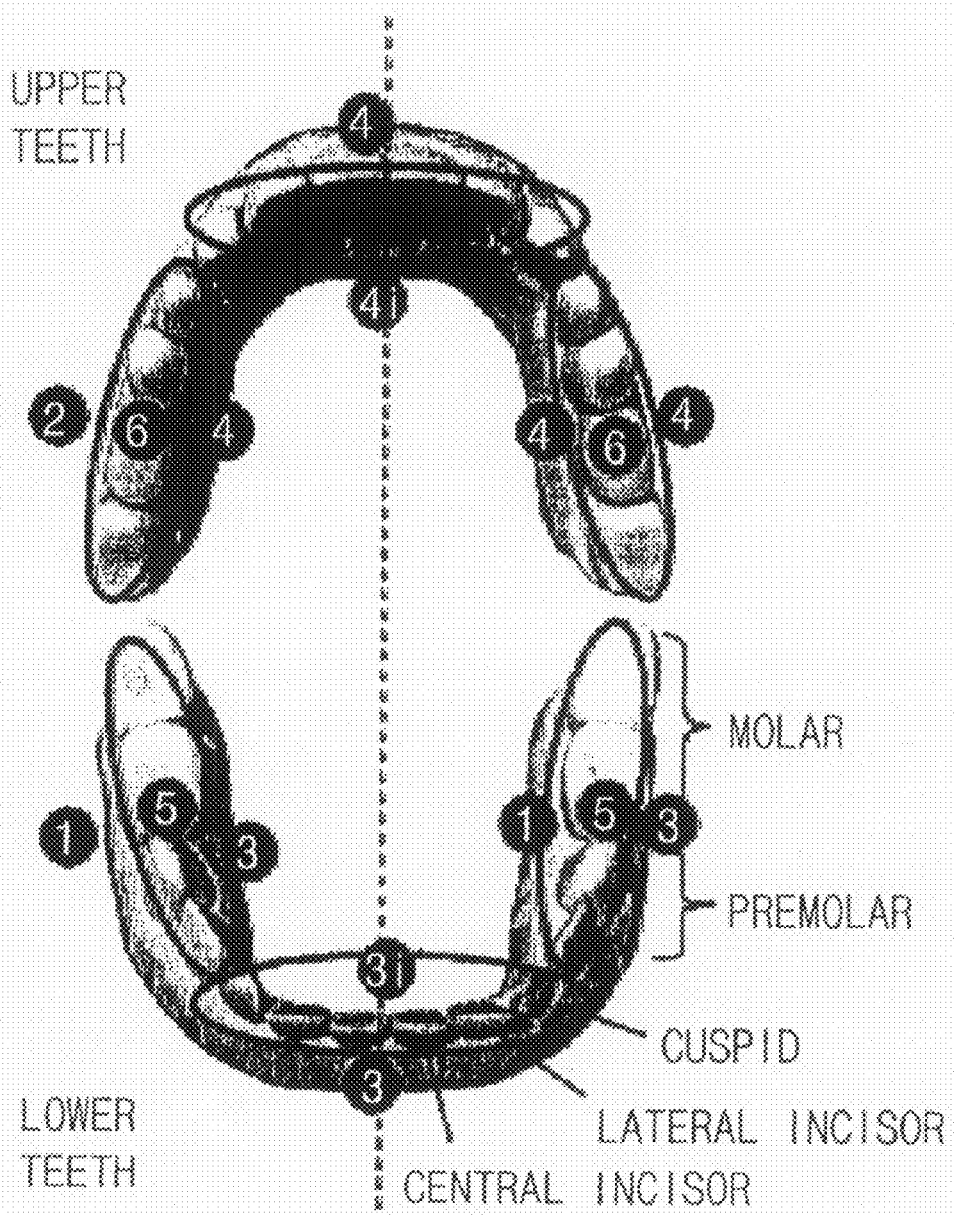
FIG. 2 is an exploded view illustrating teeth regions.

FIG. 2 is an exploded view illustrating teeth regions.

Referring to FIG. 2, teeth may be divided into six regions, that is, a lower incisor region, a lower left molar region, a lower right molar region, an upper incisor region, an upper left molar region and an upper right molar region. Each of the upper and lower incisors may be divided into an outer portion and an inner portion, and each of the right and left molars of the upper and lower molars may be divided into an outer portion, an inner portion and a bottom surface.

The user's tooth brushing pattern database 143 stores data, such as a user's tooth brushing time, tooth brushing period, tooth brushing frequency, tooth brushing angle, tooth brushing strength, tooth brushing pattern, evaluated score, and tooth brushing period of each teeth region, etc., and manages the stored data. The data may be acquired from a tooth brushing pattern analysis/correction toothbrush included in the user's system 200.

The lifetime periodic tooth brushing method database server 145 stores first proper tooth brushing method-related data, wherein the first proper tooth brushing method is recommended in accordance with average tooth formation degree and tooth shape according to age, and the second proper tooth brushing method-related data, wherein the second proper tooth brushing method is recommended in accordance with a teeth state after a dental treatment, such as prosthesis wearing, implantation, etc., and manages the data.

The personal profile database 147 stores data, such as a user's name, age, sex, address, occupation, clinical history, dental treatment status, and/or scheduled next visit, and manages the data.

The medical center profile database 149 stores data, such as a hospital's name, consultation hours, location, treatment costs, introduction, clients' evaluation scores, and/or appointment status, and manages the data.

The tooth brushing pattern analysis part 110 analyzes a tooth brushing pattern of each teeth region by analyzing a user's tooth brushing state data supplied in real-time or periodically from the user's system 200, and evaluates the analyzed results to supply the evaluated results to the tooth brushing pattern database 143.

The feedback data generation part 120, in response to the analyzed user's tooth brushing pattern, generates feedback data (including multimedia contents for tooth brushing habit correction) with reference to a user's age and lifetime periodic tooth brushing method data.

For a child, data such as a tooth brushing evaluation score, a warning sound, a guidance comment, a melody or music, an animation, etc., are fed back, or a periodic guidance comment is fed back according to number of times, day, week, month, and quarter. Simultaneously, for a guardian of the child, feedback data for monitoring is supplied. The feedback data for monitoring includes guidance data, such as a guardian's role for correcting a child's tooth brushing habits and a guiding method, or dental treatment guidance data. For a student, the feedback data for monitoring is supplied to a related school or organization so that the feedback data may be used as a tooth brushing guide.

The feedback data may include weekly measurement/analysis data, tooth brushing habit analysis data, monthly measurement/analysis data, monthly evaluation/advice data, quarterly tooth brushing habit trend data, etc.

Figure 3:
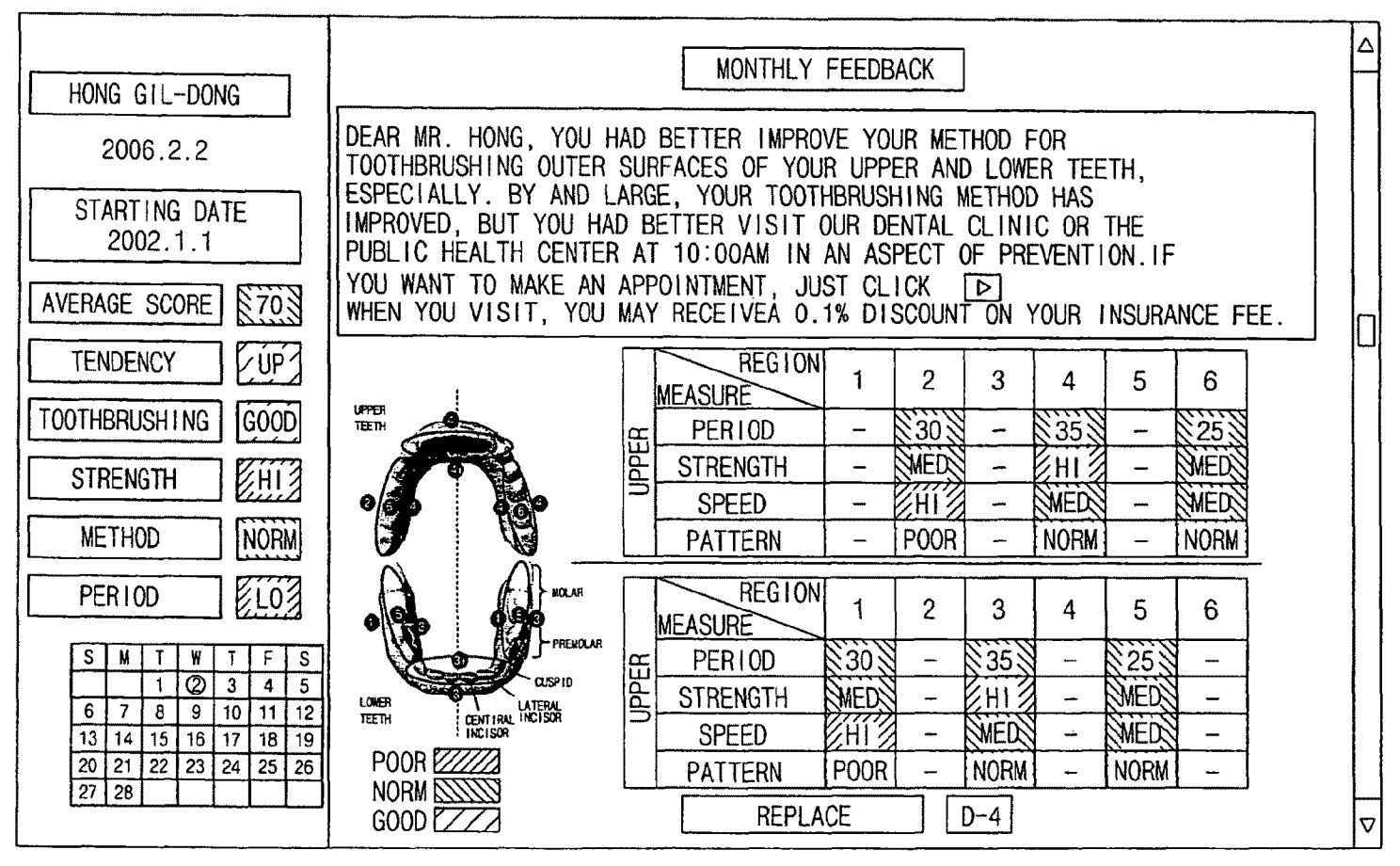

FIG. 3 is an example of monthly feedback data.

Referring to FIG. 3, the monthly feedback data includes analysis data for a bibliographical material, a user's average score, trends, tooth brushing habits, tooth brushing strength, tooth brushing period, tooth brushing pattern of each teeth region, etc., and/or guidance data.

The guidance data may include information such as an improvement degree of tooth brushing habits, whether a dental treatment is required, an appointment notification, etc.

Figure 4:
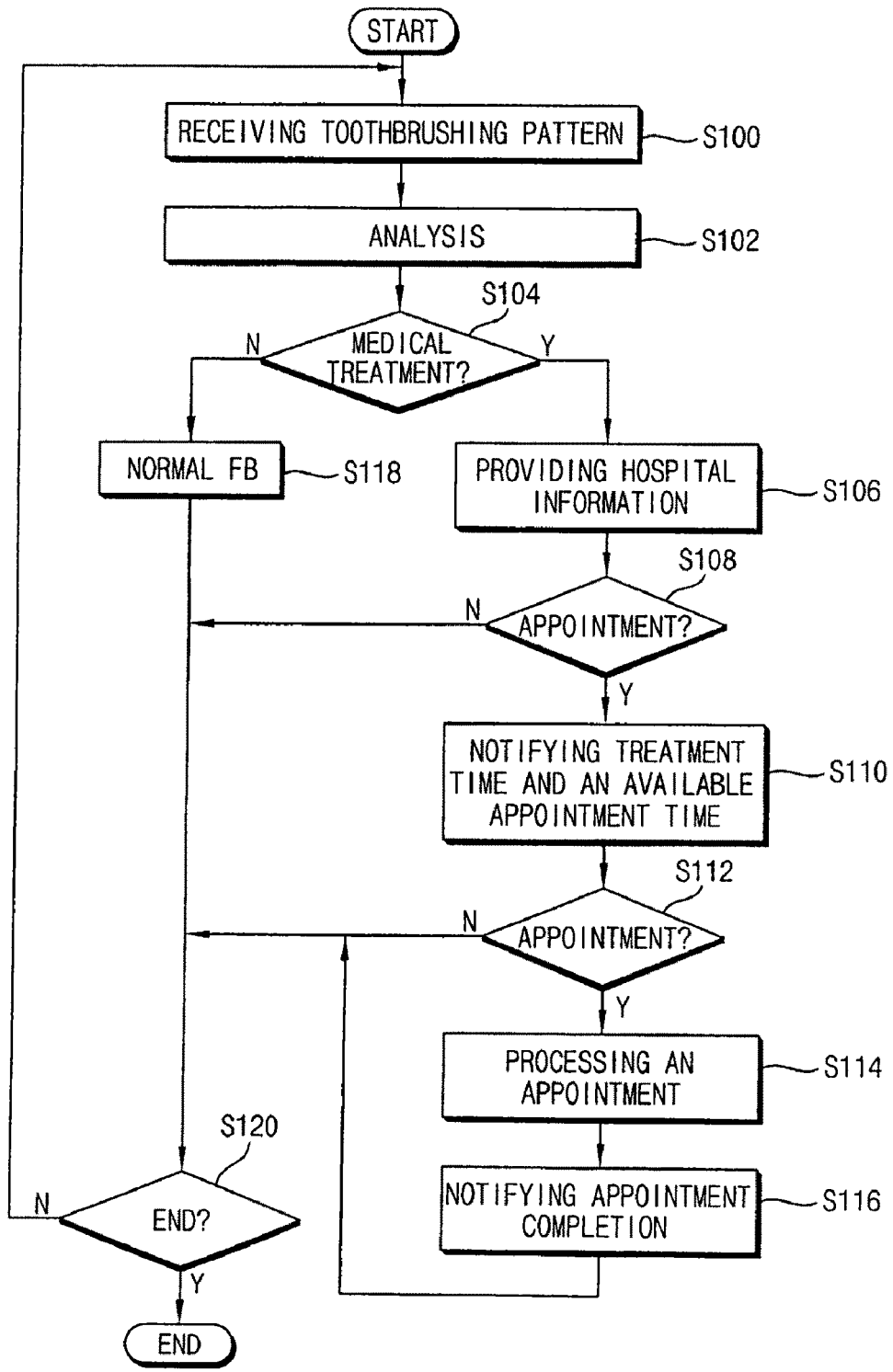
FIG. 4 is a flow chart illustrating the operation of a system for tooth brushing correction and dental appointment in accordance with an example embodiment.

FIG. 4 is a flow chart illustrating the operation of a system for tooth brushing correction and dental appointment in accordance with an example embodiment of the present invention.

Referring to FIGS. 1 and 4, in operation S100, the system 100 receives tooth brushing pattern data, and stores the tooth brushing pattern data in the tooth brushing pattern database server 143. In operation S102, the tooth brushing pattern analysis part 110 analyzes a tooth brushing pattern. The analyzed tooth brushing pattern is provided for the feedback data generation part 120. In operation S104, the personal feedback data generation part 120 generates daily feedback data and determines whether a dental treatment is needed or not. When the dental treatment is needed in operation S104, the daily feedback data is transferred to a user. In operation S106, when the user wants to make an appointment and thus clicks the appropriate selection, hospital information data available for the user are provided from the medical center profile database server 149. In operation S108, when a desired hospital is chosen, in operation S110, guidance data for a medical treatment time and available appointment times of the chosen hospital are provided. In operation S112, when the user chooses a desired appointment time, in operation S114, appointment information is transferred to the chosen hospital so that the appointment may be processed. In operation S116, when an appointment completion signal is transferred from the hospital system 300 to the system 100, the appointment completion is notified to the user.

When the dental treatment is not needed in operation S104, normal daily feedback data is provided for the user in operation S118. The system 100 may end in operation S120, or operation S100 may be repeated.

2. System for Tooth Brushing Correction and Notification of a Replacement Time of Toothbrush Bristles FIG. 5 is a block diagram of a system for tooth brushing correction and notification of a replacement time of toothbrush bristles in accordance with an example embodiment.

Figure 5:
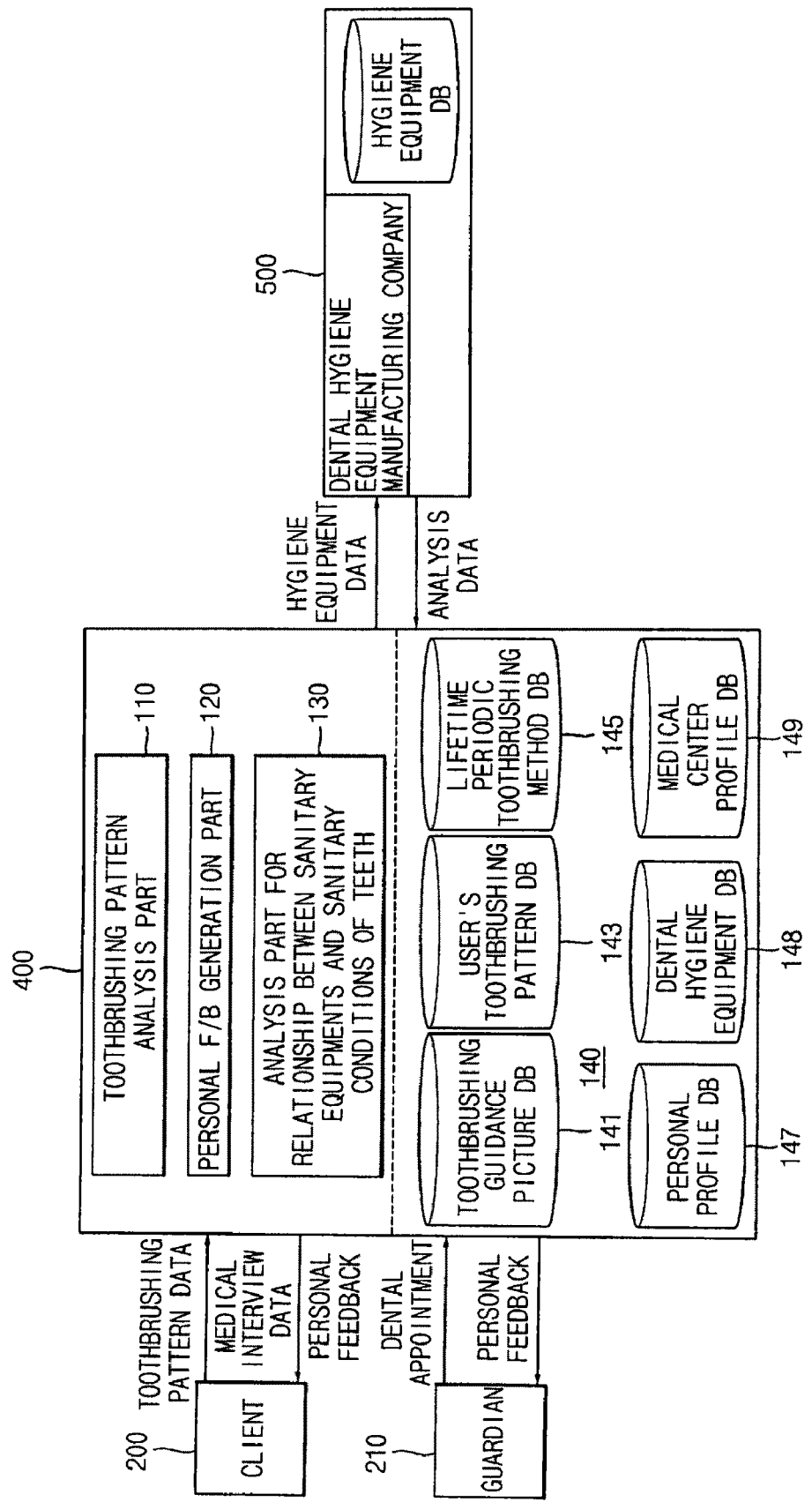
FIG. 5 is a block diagram of a system for tooth brushing correction and notification of a replacement time of toothbrush bristles in accordance with an example embodiment.

A system 400 in FIG. 5 has a difference in an aspect that the system 400 is connected to a dental hygiene equipment manufacturing/selling company system 500 instead of the medical center system 300 in order to notify a user of a replacement time of hygiene equipment such as toothbrush bristles, in comparison with the above appointment system 100.

The dental hygiene equipment manufacturing/selling company system 500 includes an affiliated dental hygiene equipment manufacturing/selling company computer system connected to the Internet, and has an application program installed therein for communicating with the system 400. The dental hygiene equipment manufacturing/selling company system 500 has a database containing product data, such as a shape of toothbrush bristles, a strength of a toothbrush, a user's age, a replacement cycle, an appearance, a size, etc. of the dental hygiene equipment, and another kind of data, such as a cost, a date of manufacture, a manufacturing company, etc.

Referring to FIG. 5, the system 400 may further include an analysis part 130 for analyzing a relationship between hygiene equipment and hygienic conditions of teeth, and a database part 140 may further include a dental hygiene equipment database 148. The other parts of the system 400 are substantially the same as those of the system 100. Thus, in FIGS. 1 and 5, the same reference numerals refer to the same elements and a further explanation will be omitted here.

Data such as purchasing time, size, cost, characteristics, strength of bristles, proper age for use, replacement cycle, shape of bristles, etc. of each piece of hygiene equipment, e.g., a toothbrush, is uploaded to the dental hygiene equipment database 148 in real-time, and the dental hygiene equipment database 148 stores and manages the data. Additionally, the database part 140 conducts quantitative and qualitative analyses for the collected user's data, and supplies analysis data for consumption states of the dental hygiene equipment according to age, sex, year, location, etc., to the manufacturing/selling company. Output control, stock management, sale strategy, etc. of the dental hygiene equipment reflect the supplied analysis data. Additionally, the database part 140 supplies analysis data for a worn state of toothbrush bristles of each kind of bristles according to age, sex, etc. to the manufacturing/selling company. The supplied data is reflected in the manufacturing of toothbrush bristles suitable to users according to age and sex.

The analysis part 130 for analyzing a relationship between hygiene equipment and hygienic conditions of teeth analyzes a user's tooth brushing habits and a user's behavior pattern stored in the user's tooth brushing pattern database, the lifetime periodic tooth brushing method database, the user's personal profile database, etc., to calculate a replacement time of a toothbrush from a purchasing time, and stores the calculated replacement time in the dental hygiene equipment database as replacement cycle data.

The replacement time may be determined with reference to data, such as a user's tooth brushing strength, tooth brushing frequency, effective tooth brushing period, total accumulated usage period, etc. The replacement time may be calculated using an accumulated value of the usage period from the last replacement time of the toothbrush bristles. Basically, a total accumulated usage period of about three months may be a criterion for determining the replacement time.

Particularly, a standard replacement time may be calculated using an accumulated tooth brushing period of about 810 minutes (3 minutes each time/3 times each day/30 days each month/3 months) as the criterion. When the user's tooth brushing strength is larger than a standard strength, the replacement time may be calculated to a value of about 70 to about 90% of the standard replacement time. On the contrary, when the user's tooth brushing strength is smaller than the standard strength, the replacement time may be calculated to a value of about 110 to about 130% of the standard replacement time.

When data for the replacement time of the toothbrush bristles are accumulated, the user's average replacement time may be regressively calculated so that an optimized replacement time for a particular user may be calculated by adding/subtracting time to/from the user's average replacement time according to measured user's tooth brushing strength.

The personal feedback data generation part 120 feeds back the calculated replacement time of the toothbrush bristles to the user and the manufacturing company so that the personal feedback data generation part 120 may advise the user and the manufacturing company to replace the toothbrush bristles. A suitable toothbrush for a user and a manufacturing company of the toothbrush may be provided to the user in response to the user's tooth brushing habits and behavior pattern. When the user shows an interest in purchasing a product in response to the advised information, purchase information is transferred to the dental hygiene equipment manufacturing/selling company system 500 so that the product purchase may be performed.

Figure 6:
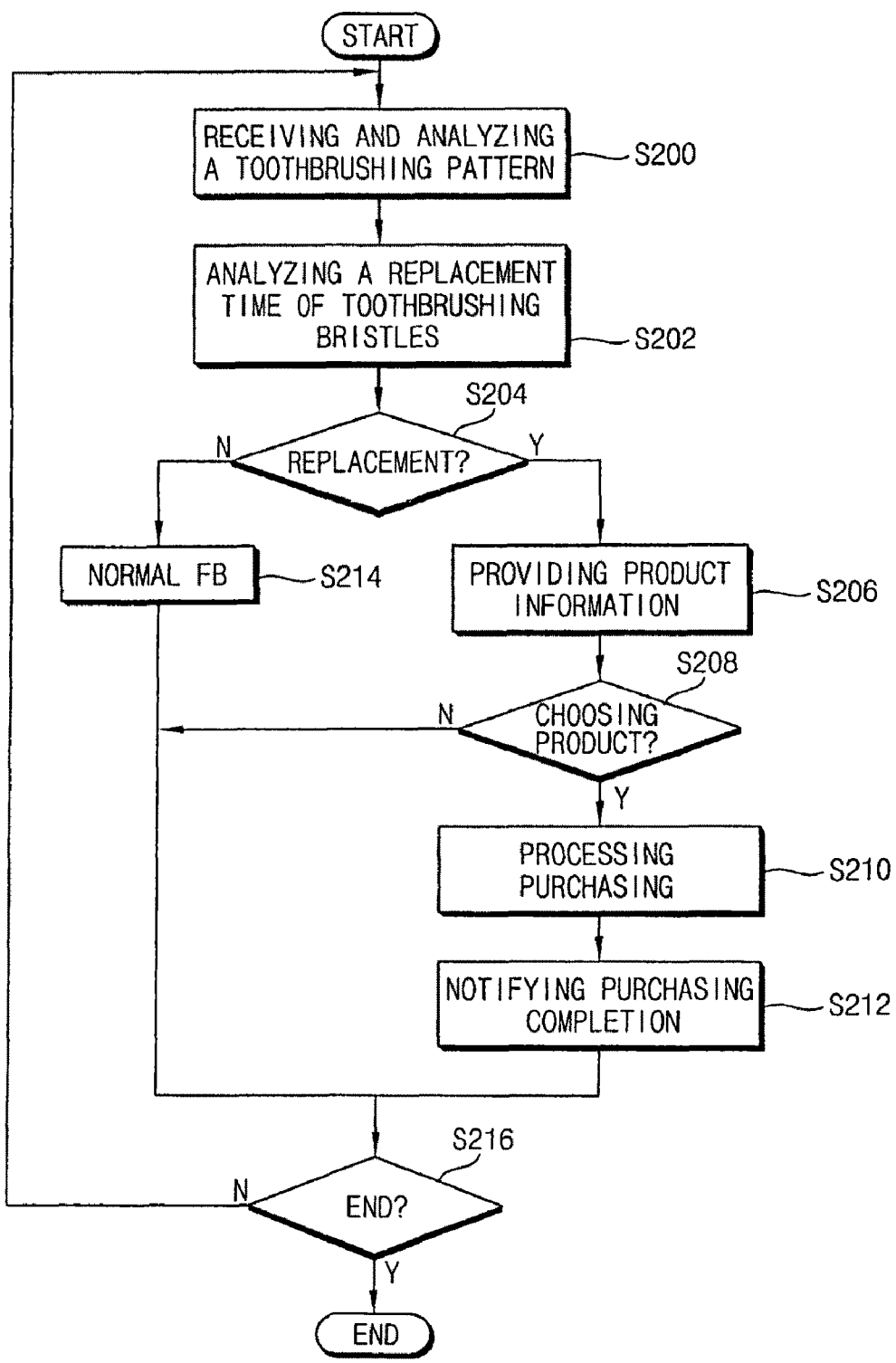
FIG. 6 is a flow chart illustrating the operation of a system for tooth brushing correction and notification of a replacement time of toothbrush bristles in accordance with an example embodiment.

FIG. 6 is a flow chart illustrating the operation of a system for tooth brushing correction and notification of a replacement time of toothbrush bristles in accordance with an example embodiment.

Referring to FIGS. 5 and 6, in operation S200, when the system receives the tooth brushing pattern data, the system 400 stores the tooth brushing pattern data in the user's tooth brushing pattern database server 143, and the tooth brushing pattern analysis part 110 analyzes a tooth brushing pattern, such as a user's tooth brushing strength, tooth brushing frequency, tooth brushing period, total accumulated tooth brushing period, adaptability, etc. The analyzed result in operation S200 is provided for the analysis part 130 for analyzing a relationship between hygiene equipment and hygienic conditions of teeth. In operation S202, the analysis part 130 for analyzing a relationship between hygiene equipment and hygienic conditions of teeth analyzes a replacement time of toothbrush bristles in response to the analyzed result. In operation S204, when the toothbrush bristles need to be replaced as a result of the analysis in operation S202, the personal feedback data generation part 120 may be advised of the replacement time. In operation S206, the personal feedback data generation part 120 transfers daily feedback data and guidance data for product information, which are transferred from the dental hygiene equipment database, to the user. Additionally, information of the most suitable toothbrush bristles for the user may be provided for the user. In operation S208, when the user chooses a certain product with reference to provided information, in operation S210, choice data for the chosen product is provided for the dental hygiene equipment manufacturing/selling company system 500 so that product purchase may be performed. In operation S212, when a product purchase completion signal is transferred from the dental hygiene equipment manufacturing/selling company system 500 to the system 400, product purchase completion is notified to the user. When product purchase completion is notified to the user, characteristics of the purchased toothbrush bristles and correct tooth brushing methods in accordance with the user's tooth brushing pattern may be notified to the user.

When the replacement of the toothbrush bristles is not needed in operation S204, normal daily feedback data is provided for the user in operation S214. The system 400 may end in operation S216, or operation S200 may be repeated.

3. System for Tooth Brushing Correction and Insurance Management

Figure 7:
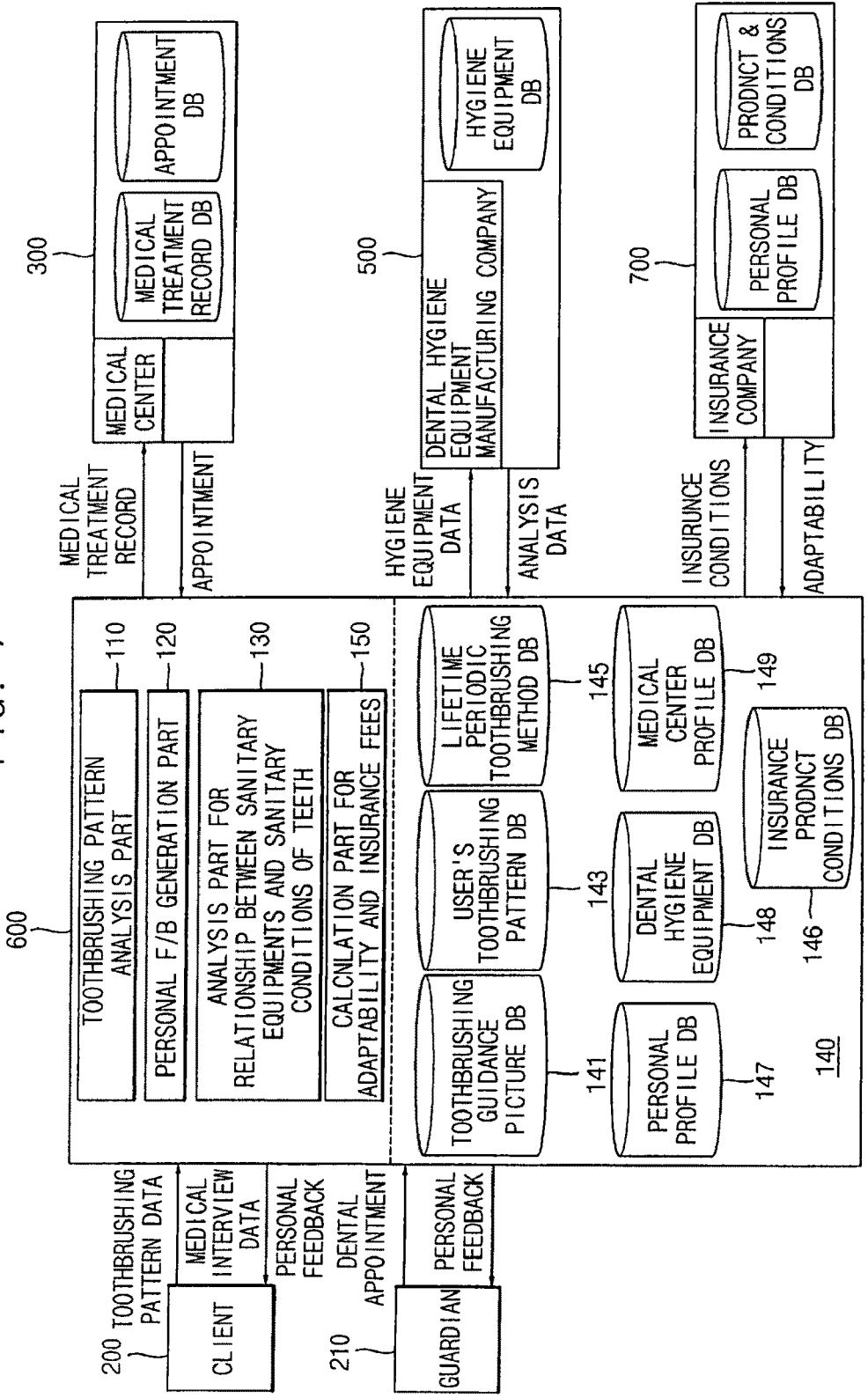
FIG. 7 is a block diagram of a system for tooth brushing correction and insurance management in accordance with an example embodiment.

FIG. 7 is a block diagram of a system for tooth brushing correction and insurance management in accordance with an example embodiment. A system 600 in FIG. 7 has a difference in an aspect that the system 600 is connected to an insurance system 700 instead of the medical center system 300 in order to manage an insurance rate according to a user's tooth brushing habit adaptability, in comparison with the above appointment system 100.

Referring to FIG. 7, the system 600 may further include a calculation part 150 for adaptability and insurance fees, and the database part 140 may further include an insurance product conditions database server 146. The other parts of the system 600 are substantially the same as those of the system 100. Thus, in FIGS. 1 and 7, the same reference numerals refer to the same elements and a further explanation will be omitted here.

The system 600 may feedback a fluctuation state of an insurance rate in accordance with a user's tooth brushing habits to lead the user into correct tooth brushing habits and accurately calculate an insurance fee.

An oral insurance fee may be set and controlled in relation to a user's changing information, such as a tooth brushing pattern, a tooth-related prescription, a change of an inner structure of a tooth, etc., according to predetermined criteria.

The insurance product conditions database 146 stores and manages data, such as tooth-related insurance products, insurance rates, tooth-related insurance fee premium/discount factors, the number of dental treatments, etc.

Here, the tooth-related insurance fee premium/discount factors may include one or more of the following factors:

1. User's Tooth Brushing Data

User's total enrollment period (data transfer period)

Poor/good tooth brushing pattern number of times/each time

Poor/good tooth brushing period/each time

Tooth brushing strength

Tooth brushing speed

Tooth brushing period

Average number of tooth brushings each day (weekly, monthly, quarterly)

Average period of tooth brushings, average score of tooth brushings

Weekly/monthly data transfer rate

Date

Kind of toothbrush bristles used

Tooth brushing location

2. User's Personal and Environmental Information

User's bibliographic information (age, sex, etc.)

Cohabitant

Cohabitant's dental state

User's diagnosis, examination and treatment (prescription) data

User's dental disease-related direct/indirect history

User's dental state

3. Toothbrush Bristles

Using a recommended product or not

Observing a correct replacement time or not

In order to determine whether a premium or a discount is needed or not by analyzing the above factors, the following premium/discount evaluation items are calculated.

1. Premium

Less than 1 time of average number of tooth brushing each day

Greater than 6 times of number of tooth brushings a day

Less than 30 seconds of average tooth brushing period

Less than 50% of average data transfer rate

Greater than 50% of poor tooth brushing pattern time during each brushing time

2. Discount

Greater than 90% of average data transfer rate

Greater than 90% of number of tooth brushing having score around average tooth brushing score Greater than 90 points of average tooth brushing score Above 3 minutes of average tooth brushing period.

Insurance rank factors and premium/discount factors may have some common factors. Actually, until the tooth brushing pattern data is collected and analyzed, whether the user's information will be used as the insurance factors or the premium/discount factors may not be determined. However, according to some example embodiments, the user may accurately understand the user's tooth brushing pattern so that the actual user's information may be made based on the insurance fee. Further, errors of the insurance rank may be prevented from occurring and the insurance rank may be subdivided. Furthermore, an insurance fee, which may be directly controlled, may be determined by the user.

The calculation part 150 for adaptability and insurance fees takes user's tooth brushing correction data stored in the user's tooth brushing pattern database, the lifetime periodic tooth brushing method database, the personal profile database, etc., and calculates tooth brushing correction adaptability with reference to the above evaluation items. Additionally, the calculation part 150 for adaptability and insurance fees calculates a fluctuation of an insurance rate according to evaluation of the adaptability for a predetermined time, and calculates an insurance fee in accordance with the evaluated results.

When the calculated adaptability and the insurance fee are determined to be changed, the personal feedback data generation part 120 feeds back tooth brushing guidance data that warn the user of an insurance rate increase by feeding back warning and guiding comments to the user. Additionally, the personal feedback data generation part 120 calculates an insurance rate from the accumulated data for a predetermined time so that the personal feedback data generation part 120 advises the user of the calculated insurance rate. Thus, the tooth brushing guidance data fed back to the user may contribute to leading the user's tooth brushing habits into being corrected toward an insurance rate to be decreased. Additionally, the system and the method in accordance with some example embodiments of the present invention may be applicable in managing a medical life cooperative in a form similar to insurance. Further, the system and the method may change or maintain a monthly membership fee of a user according to the user's tooth brushing pattern adaptability.

Figure 8:
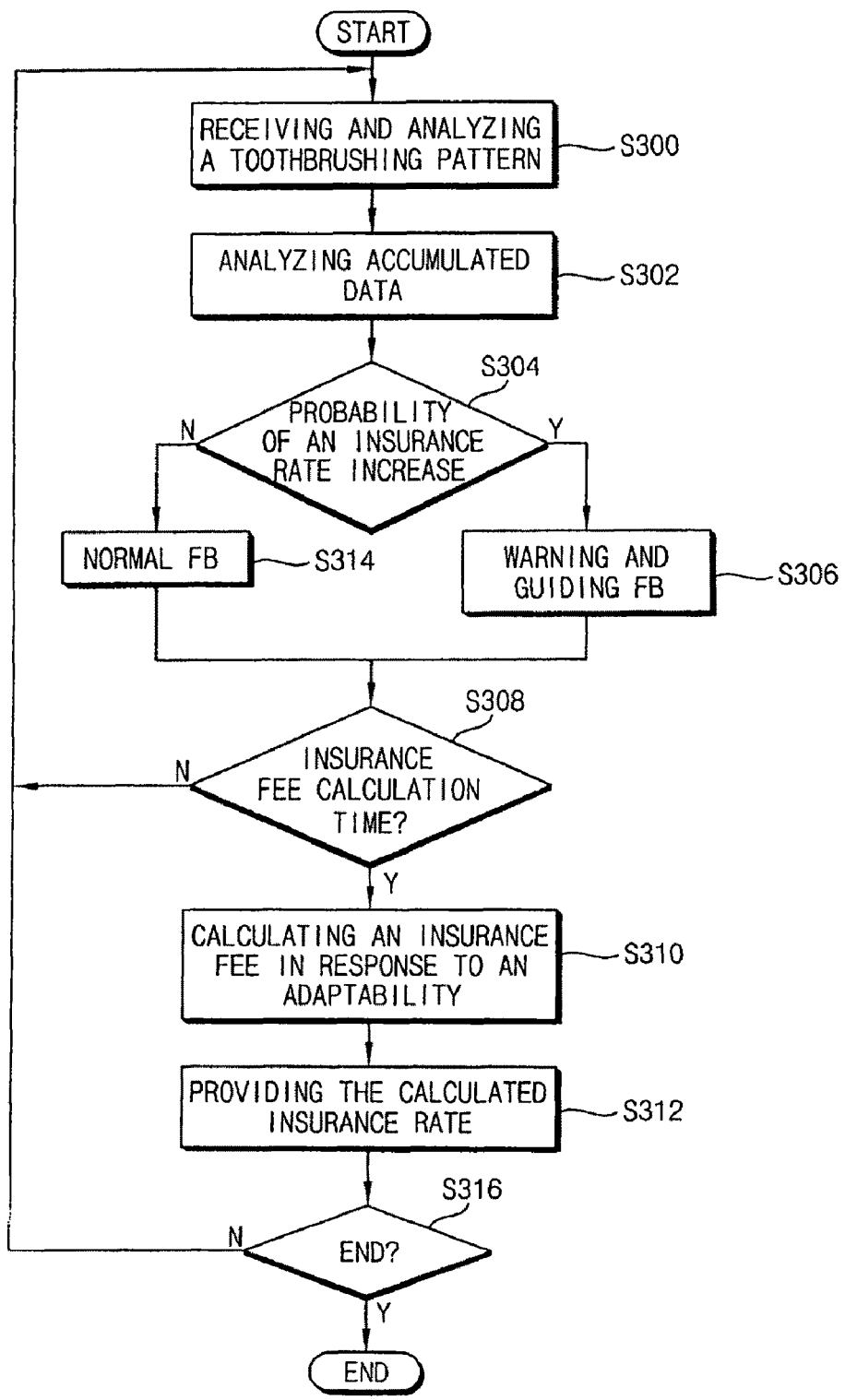
FIG. 8 is a flow chart illustrating the operation of a system for tooth brushing correction and insurance management in accordance with an example embodiment.

FIG. 8 is a flow chart illustrating the operation of a system for tooth brushing correction and insurance management in accordance with an example embodiment of the present invention.

Referring to FIGS. 7 and 8, in operation S300, when the system 600 receives tooth brushing pattern data, the tooth brushing pattern database server 143 stores the tooth brushing pattern data, and the tooth brushing pattern analysis part 110 analyzes the tooth brushing pattern. In operation S302, when accumulated results analyzed in operation S300 are provided for the calculation part 150 for adaptability and insurance fees, the calculation part 150 for adaptability and insurance fees analyzes the accumulated results to calculate whether the adaptability and the insurance fee may be changed. In operation S304, a probability of the insurance rate increase is checked in response to the above calculation. When the probability of the insurance rate increase is determined to be high, that is, the above premium factor is checked, in operation S306, the determined result is provided for the personal feedback generation part 120, and the personal feedback generation part 120 warns or sends guidance comments that the insurance rate may be increased for the user with daily feedback data. In operation S308, whether a predetermined time has been reached for calculating the insurance rate or not is checked. When the predetermined time for calculating the insurance rate has been reached, in operation S310, the insurance rate is calculated in response to the user's adaptability. In operation S312, the calculated insurance rate is provided for the user so that the user may be notified.

When the probability of the insurance rate increase is low, normal daily feedback data is provided for the user in operation S314. The system 600 may end in operation S316, or operation S300 may be repeated.

This invention has been described with reference to the example embodiments. It is evident, however, that many alternative modifications and variations will be apparent to those having skill in the art in light of the foregoing description. Accordingly, the present invention embraces all such alternative modifications and variations as falling within the spirit and scope of the appended claims.

INDUSTRIAL APPLICABILITY

According to an embodiment, a system is provided in which systematical oral health management may be performed by organically linking a person, a home, a school, a dental hospital, a toothbrush manufacturing/selling company, a public health center, an insurance company, etc. to one. Additionally, according to the present invention, a user may be lead into acquiring correct tooth brushing habits so that the user may manage the user's oral health with an economical insurance fee. Further, efficient manufacturing/sales for dental hygiene equipment may be induced, and a dental hospital may have increased earnings.

Although a few embodiments have been shown and described, it would be appreciated by those skilled in the art that changes may be made in these embodiments without departing from the principles and spirit of the invention, the scope of which is defined in the claims and their equivalents.

The invention claimed is:

1. A method of managing of oral care for a tooth brushing correction and insurance management system comprising:
    receiving tooth brushing pattern data generated when a user uses a tooth brushing correction toothbrush;
    storing the received tooth brushing pattern data in a user's tooth brushing pattern database to a database;
    analyzing the stored tooth brushing pattern data with reference to information of the user by a tooth brushing pattern analyzer;
    determining a probability of an insurance rate increase according to the analyzed result of the stored tooth brushing pattern data being done by a computer;
    warning the user of the probability of the insurance rate increase when the insurance rate is expected to increase by the determination;
    calculating an adaptability of the user by the analyzed result being done by the computer;
    calculating an insurance rate of the user in response to the adaptability; and
    providing the calculated insurance rate to the user,
    wherein the tooth brushing pattern data comprises a tooth brushing period of each teeth region comprises at least four of a lower incisor region, a lower left molar region, a lower right molar region, an upper incisor region, an upper left molar region and an upper right molar region.

2. The method of claim 1, wherein the tooth brushing pattern data further comprises any one of upward and downward motion, back-and forth motion, clockwise motion, counterclockwise motion and rotational motion along the respective tooth location.

3. The method of claim 1, wherein the analyzed result further comprises any one of poor/good tooth brushing pattern number of times/each time, tooth brushing period, average period of tooth brushings, average score of tooth brushings, tooth brushing speed, and poor/good tooth brushing period/each time.

4. The method of claim 1, calculating an adaptability of the user by analyzing the tooth brushing pattern data and enrollment conditions.

5. The method of claim 1, wherein providing normal daily feedback data when the probability of the insurance rate increase is low, instead of warning the user of the probability of the insurance rate increase.

6. The method of claim 1, further comprising:
    providing feedback data comprising any one of poor/good tooth brushing pattern number of times/each time, tooth brushing period, average period of tooth brushings, average score of tooth brushings, tooth brushing speed, and poor/good tooth brushing period/each time by a personal feedback generator.

7. The method of claim 1, wherein each of the lower incisor region, the lower left molar region, the lower right molar region, the upper incisor region, the upper left molar region and the upper right molar region is divided into an outer portion and an inner portion.

8. A method of managing of oral care for a tooth brushing correction and insurance management system comprising:
- receiving tooth brushing pattern data generated when a user uses a tooth brushing correction toothbrush;
- storing the received tooth brushing pattern data in a user's tooth brushing pattern database to a database;
- analyzing the stored tooth brushing pattern data with reference to information of the user by a tooth brushing pattern analyzer;
- determining an insurance rate according to the analyzed result of the stored tooth brushing pattern data being done by a computer;
- warning the user of the probability of the insurance rate increase when the insurance rate is expected to increase by the determination;
- calculating an adaptability of the user by the analyzed result being done by the computer;
- calculating an insurance rate of the user in response to the adaptability;
- providing the calculated insurance rate to the user;
- determining whether a dental treatment for the user is needed or not according to the analyzed result by the personal feedback generator part; and
- providing information of a treatment hospital and an available appointment time of the treatment hospital from a medical center profile database for the user when the dental treatment for the user is needed by the personal feedback generator part.

9. The method of claim 8, further comprising:
processing an appointment of the user at the appointment time in the treatment hospital chosen by the user in response to the provided information by the personal feedback generator.

10. The method of claim 8, further comprising:
analyzing a relationship between hygiene equipment and hygienic conditions of teeth, determining a replacement time of dental hygiene equipment of the user according to the analyzed result by the analyzer; and
providing information of a product for the user when the dental hygiene equipment needs to be replaced by a personal feedback generator.

11. The method of claim 10, further comprising:
processing purchasing of a product by the personal feedback generator, wherein the product is chosen by the user among the products whose information of a hygiene equipment DB is provided for the user.

\* \* \* \* \*